(12) United States Patent
Vogtmeier et al.

(10) Patent No.: US 12,622,597 B2
(45) Date of Patent: May 12, 2026

(54) MEDICAL IMAGING METHOD WITH GUIDANCE

(71) Applicant: KONINKLIJKE PHILIPS N.V., Eindhoven (NL)

(72) Inventors: Gereon Vogtmeier, Aachen (DE); Steffen Weiss, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 154 days.

(21) Appl. No.: 18/565,095

(22) PCT Filed: May 25, 2022

(86) PCT No.: PCT/EP2022/064156
§ 371 (c)(1),
(2) Date: Nov. 29, 2023

(87) PCT Pub. No.: WO2022/253657
PCT Pub. Date: Dec. 8, 2022

(65) Prior Publication Data
US 2024/0252056 A1     Aug. 1, 2024

(30) Foreign Application Priority Data

Jun. 4, 2021     (EP) ..................................... 21177673

(51) Int. Cl.
A61B 5/055          (2006.01)
A61B 5/00            (2006.01)
(Continued)

(52) U.S. Cl.
CPC .............. A61B 5/055 (2013.01); A61B 5/721 (2013.01); A61B 5/7485 (2013.01);
(Continued)

(58) Field of Classification Search
None
See application file for complete search history.

(56) References Cited

U.S. PATENT DOCUMENTS

| | | | |
|---|---|---|---|
| 11,609,295 B2 * | 3/2023 | Koerzdoerfer | ..... G01R 33/4835 |
| 2004/0116804 A1 * | 6/2004 | Mostafavi | .............. A61B 6/541 |
| | | | 600/428 |

(Continued)

FOREIGN PATENT DOCUMENTS

| | | | | |
|---|---|---|---|---|
| DE | 102014207295 A1 * | 10/2015 | ............. | A61B 5/055 |
| EP | 3581109 A1 | 12/2019 | | |

(Continued)

OTHER PUBLICATIONS

International Search Report and Written Opinion from PCT/EP2022/064156 mailed Aug. 17, 2022.

*Primary Examiner* — Rodney E Fuller

(57) ABSTRACT

A medical imaging system is operated by determining a positioning rule indicating, for a region of interest, a target position, wherein a deviation between an actual position and the target position can affect imaging performance; obtaining measurement data of the region of interest, from which the actual position of the region of interest is derivable; determining a current deviation between the actual position and the target position of the region of interest, by comparing the positioning rule with the obtained measurement data; generating imaging performance information indicating whether the current deviation between the actual position and the target position of the region of interest currently affects the imaging performance in terms of image quality and/or remaining imaging time, or is expected to affect the imaging performance in terms of quality and/or remaining imaging time; and providing the generated imaging performance information to be communicated to a subject to be imaged.

15 Claims, 2 Drawing Sheets

(51) Int. Cl.

| | | |
|---|---|---|
| *G01R 33/54* | (2006.01) | |
| *G01R 33/56* | (2006.01) | |
| *G01R 33/565* | (2006.01) | |
| *G16H 40/63* | (2018.01) | |
| *G16H 70/20* | (2018.01) | |

(52) U.S. Cl.

CPC ....... *G01R 33/546* (2013.01); *G01R 33/5608* (2013.01); *G01R 33/56509* (2013.01); *G16H 40/63* (2018.01); *G16H 70/20* (2018.01)

(56) References Cited

U.S. PATENT DOCUMENTS

| | | | |
|---|---|---|---|
| 2005/0283068 A1 | 12/2005 | Zuccolotto et al. | |
| 2011/0112351 A1* | 5/2011 | Fordyce | A61N 5/103 |
| | | | 600/1 |
| 2013/0211261 A1* | 8/2013 | Wang | G16H 50/30 |
| | | | 600/476 |
| 2014/0029828 A1 | 1/2014 | Schwartz et al. | |
| 2015/0045654 A1 | 2/2015 | Lee et al. | |
| 2015/0196780 A1* | 7/2015 | Tijs | A61N 5/1049 |
| | | | 600/1 |
| 2015/0208981 A1 | 7/2015 | Oh et al. | |
| 2015/0352375 A1* | 12/2015 | Chen | A61N 5/1049 |
| | | | 600/1 |
| 2016/0235335 A1 | 8/2016 | Kim et al. | |
| 2017/0231530 A1 | 8/2017 | Kim et al. | |
| 2017/0319814 A1 | 11/2017 | Giap et al. | |
| 2019/0261940 A1* | 8/2019 | Son | G06T 11/008 |
| 2021/0244283 A1* | 8/2021 | Krueger | A61N 5/1048 |
| 2022/0015722 A1* | 1/2022 | Chaudhury | G16H 40/63 |
| 2022/0125395 A1* | 4/2022 | Burbar | A61B 6/0407 |

FOREIGN PATENT DOCUMENTS

| | | | | |
|---|---|---|---|---|
| EP | 3666334 A1 | 6/2020 | | |
| WO | WO-2013159787 A1 * | 10/2013 | ........... | A61N 5/1049 |

* cited by examiner

MEDICAL IMAGING METHOD WITH GUIDANCE

CROSS REFERENCE TO RELATED APPLICATIONS

This application is a U.S. national phase application of International Application No. PCT/EP2022/064156 filed on May 25, 2022, which claims the benefit of EP application Ser. No. 21/177,673.7 filed on Jun. 4, 2021 and is incorporated herein by reference.

FIELD OF THE INVENTION

The present invention relates to medical imaging, and in particular to a computer-implemented method for operating a medical imaging system, a medical imaging system, and a computer program element.

BACKGROUND OF THE INVENTION

In medical imaging, particularly within a medical imaging facility, it is desired to have a patient throughput that is as high as possible. At the same time, image quality should be as good as possible, which are conflicting goals. In practice, these conflicting goals may be addressed by instructing the patient prior to the actual imaging procedure, particularly the actual image acquisition, by medical professionals to support or help as much as possible, e.g., to suppress or avoid movements, so that the image quality is as high as possible. For example, the patient may be informed about e.g. what actions during the imaging procedure are requested to arrive at a suitable image quality for facilitated diagnosis and/or a high image quality. In some cases, the patient may think of having a good understanding of the imaging procedure and/or what will happen and what is expected from the patient. However, in at least some cases, the patient might have overseen something or just misunderstood some information regarding a behavior of the patient during individual imaging procedure steps, which, in the case of e.g. unwanted movements, etc., can result in reduced image quality and/or, e.g. if an image acquisition has to be repeated as a result of insufficient cooperation or performance of the patient, in lower patient throughput in the medical imaging facility.

SUMMARY OF THE INVENTION

There may, therefore, be a need for improved means for guiding a subject undergoing a medical imaging procedure. The object of the present invention is solved by the subject matter of the independent claims, wherein further embodiments are incorporated in the dependent claims.

According to a first aspect, there is provided a method for operating a medical imaging system. The method comprises:

determining, by a data processing unit, a positioning rule, at least indicating, at least for a region of interest, one or more target positions, wherein a deviation between an actual position and the target position can affect imaging performance;

obtaining, by the data processing unit, measurement data of at least the region of interest, to derive the actual position of at least the region of interest;

determining, by the data processing unit, a current deviation between the actual position and the target position of at least the region of interest, by comparing the positioning rule with the obtained measurement data;

generating, by the data processing unit, imaging performance information, at least indicating whether the current deviation between the actual position and the target position of at least the region of interest currently affects the imaging performance in terms of image quality and/or remaining and/or total imaging time or not, or is expected to affect the imaging performance in terms of image quality and/or remaining and/or total imaging time or not; and providing, by the data processing unit, the generated imaging performance information to be communicated to a subject to be imaged.

In this way, the subject may be informed and/or guided by automatic and/or computational means, in order to assist, by providing the generated imaging performance information to the subject, the subject in supporting the medical imaging procedure as vigorously as possible and as intended. This includes, at the subject's side, to adhere as consistently as possible to a predetermined plan and/or guideline for the medical imaging procedure to be performed at the subject, e.g. a behavior guideline, imaging plan, scan protocol, etc., that is adapted to the medical imaging procedure to be performed. As the imaging performance information is updated in content from time to time, e.g. is periodically updated, the subject receives guidance based on the subject's actual performance in supporting the medical imaging procedure. Likewise, changes in the subject's performance in supporting the medical imaging procedure may be automatically detected and, in response to this change, the imaging performance information may be changed or adapted accordingly. This assists a fast execution of the imaging procedure, meaning a high throughput of subjects in a medical imaging facility, by providing the imaging performance information, allowing for a precise and fast determination of the subject's actions and also besides the qualitative information a quantitative value and/or quantitative measure for a qualitative. Further, this also assists quantitative feedback how well the subject complies with the individual procedure steps during the medical imaging procedure. The feedback on imaging performance in terms of e.g. image quality and/or remaining imaging time when considering the positive and/or negative compliance of the subject and allows the subject to actively affect or influence the imaging procedure including procedure or imaging time and/or image quality.

In other words, the imaging performance information may be estimated and/or predicted based on the current deviation between actual and target positioning, and may be indicative for an actual compliance, e.g. with a guideline, plan and/or protocol, for or with the planned medical imaging procedure to be performed and/or currently performed at the subject, of the subject's performance in supporting the medical imaging procedure. The actual compliance may be understood as the subject's performance versus the planned and/or proposed image acquisition or scan.

Preferably, the method may be computer-implemented. Further preferably, the medical imaging system may be operated and/or a medical imaging procedure carried out by utilizing the medical imaging system may be performed in an autonomous operating mode. This may be a semi-autonomous operating mode, in which one or more, but not all, imaging procedure steps are supported by human intervention, e.g. by medical staff or technicians, and one or more, but not all, imaging procedure steps are performed in an automatic manner by the medical imaging system, or which may be a fully-autonomous operating mode, in which at least the actual medical imaging procedure, particularly the actual image acquisition, is carried out without human intervention but automatically by the medical imaging system. Optionally, the fully-autonomous operating mode may also concern one or more steps of the imaging procedure in general, such as preparation of the subject, by providing an automatic guidance or the like to the subject. The medical imaging system may be a magnetic resonance imaging (MRI) system, a magnetic resonance (MR) LINAC system, a PET-MR, or another MR-hybrid system.

As used herein, the positioning rule may comprise information about and/or a specification on a workflow of the imaging procedure to be performed at or on the subject. It may comprise information about how the subject should desirably or ideally behave during one or more steps of the imaging procedure, which steps may also be specified in the positioning rule. For example, the positioning rule may comprise information which position is to be taken, held or changed by the subject with reference to one or more steps of the imaging procedure. Alternatively or additionally, the positioning rule may comprise information about a desired or ideal breathing behavior, such as which breathing activity, breathing inactivity and/or breathing pattern is to be performed by the subject with reference to one or more steps of the imaging procedure. The positioning rule may be assigned to a specific region of interest of the subject to be imaged. It is noted that a deviation between an actual position of the subject and the target position specified in the positioning rule can affect imaging performance, because image quality may be reduced, e.g. due to undesired motion, displacement from ideal position, etc., of the subject, and/or the time required for the imaging procedure may be increased, e.g. due to repetition of one or more imaging procedure steps.

As used herein, the measurement data may be obtained by one or more detection means, such as a sensor, camera, etc. It may be assigned to one or more regions of interest to be imaged. By processing the measurement data by using a data processing unit, the actual position may be determined, i.e. derived.

Further, as used herein, the imaging performance information, which may also be referred to as an imaging performance feedback, may be configured to indicate, based on the determined current deviation, how the well the subject's behavior meets the requirements of a current step of the imaging procedure, wherein the requirements are specified in the positioning rule. For example, the imaging performance information may comprise a quantitative feedback, i.e. a meaningful figure or image, and/or a qualitative feedback associated with the current subject's performance in supporting the current step of the imaging procedure. Further, the imaging performance information may comprise guidance information determined, e.g. calculated, to assist, by means of a notification to the subject, the subject to change and/or adapt its current behavior in a manner to improve meeting the requirements set out in the positioning rule. The imaging performance information may further comprise a prediction of what imaging performance may be expected when the current performance of the subject during the imaging procedure (step), such as mispositioning and/or motion etc., would be maintained. Further, the effect of a current motion of the subject on the image may be realistic, exaggerated, or underrepresented in the imaging performance information, depending on an actual amount of motion of the subject. This ensures that image quality of the figures or images presented for guidance is on a minimum level such that the subject can at least recognize basic anatomical features in these figures or images.

As used herein, the communication of the imaging performance information may be communicated to the subject in a manner perceptible to the subject. This may contain visual, audio, tactile, etc. communication by using respective communication means, such as a display, loudspeaker, headphone, etc.

According to an embodiment, the generated imaging performance information comprises a first indicator associated with a measure, e.g. quantitative or qualitative measure, of image quality of the imaging to be expected with the current deviation. In other words, the effect of the level or degree of compliance on the image quality may also directly demonstrated, e.g. by means of visualization or the like, to the subject to boost the motivation to comply with the requirements of the imaging procedure (step).

In an embodiment, the generated imaging performance information may comprise a second indicator associated with a measure, e.g. quantitative or qualitative measure, of a remaining and/or total imaging time and/or scan time of the imaging to be expected with the current deviation. For example, the expected scan time may be communicated, e.g. by visualization, to the subject. In this way, a direct feedback, particularly by visualization, on gross motion and breathing motion, which represents detailed guidance for the subject of how to comply best, can be provided to the subject.

According to an embodiment, the generated imaging performance information may comprise at least one artificial image estimated for the case that the current deviation is maintained or at least not reduced to an allowed threshold. For this purpose, one or more images with more or less image quality may be visualized, e.g. displayed etc., to the subject in at least near real-time, depending on the level or degree of compliance. This allows an intuitive understanding of the subject of how much its current compliance affects image quality. The subject may understand this mechanism similarly as it knows how holding e.g. a photo camera still relates to the sharpness of a picture that is taken. For example, the one or more images may be based on data actually acquired from the present subject. For example, various types of scans may show anatomical detail as scans with T1-weighting or T2-weighting. This may not be done for pure functional scans as diffusion scans because they cannot be easily interpreted or recognized by the subject as a layman. In these cases, rather anatomical scans of the same body region may be displayed. In this way, a direct and intuitive feedback, particularly by visualization, on gross motion and breathing motion, which represents guidance for the subject on how to comply best, can be provided to the subject.

In an embodiment, the at least one artificial image may be estimated from one or more pre-recorded images of the same or similar region of interest acquired at a previous subject. Thereby, the one or more images demonstrated, e.g. displayed, to the subject may be a pre-recorded image of the same body part, i.e. the region of interest, but acquired in the past from other patients, which will hardly be noticeable for the subject. Therefore, the one or more images may also be referred to as a synthesized image, since this is not actually acquired from the present subject. For synthesizing the one or more images, one or more data manipulation techniques known in the art, such as techniques in k-space, may be used to determine, e.g. calculate, one single image or a series of images with different levels of motion artefacts from one base image, preferably, a high quality base image. At least one of these images may be displayed at a time depending on the current level or degree of motion/deviation from ideal position as set out in the positioning rule. In this way, a direct feedback, particularly by visualization, on gross motion and/or breathing motion, which represents detailed guidance for the subject of how to comply best, can be provided to the subject.

According to an embodiment, the generated imaging performance may comprise one or more instructions for one or more actions, configured to instruct the subject to at least reduce the current deviation by carrying out the one or more actions, i.e. to provide guidance to achieve the target position from the actual position. The one or more instructions may be communicated to the subject by one or more of visualization, in audio, by tactile communication, or the like. For example, it may comprise a command and/or guidance according to which at a certain time, for example at this moment, as soon, etc., a certain movement, e.g. breathing movement, is to be performed, a movement is to be avoided, or the like. Further, a dynamic display algorithm may focus on the most critical non-compliant performance and may give support information and/or guidance to the subject to go back on track, i.e. increase compliance with the requirements of the imaging procedure. Furthermore, for breathing frequency synchronization, for example, a visual signal, e.g. display, and/or audio signal with iterative adaptation of the frequencies may guide the subject to a target frequency. In this way, the subject can be automatically instructed and/or guided to better comply with the requirements of the imaging procedure, i.e. the positioning rule, and the imaging procedure can be supported automatically.

In an embodiment, providing the generated imaging performance information may comprise visualizing the same for the subject. For this purpose, a device for carrying out the method and/or the medical imaging system carrying out the method may comprise means for visualization such as one or more displays, or the like. In this way, the imaging performance information can be perceived more clearly or intuitively by the subject and the imaging procedure can be supported automatically.

According to an embodiment, the imaging performance information may be generated with a refresh rate adapted to a current stage of the imaging procedure, i.e. with a refresh rate adapted to a scan protocol. For example, the imaging performance information may be updated from time to time, wherein the refresh rate may be adapted to the overall imaging procedure or to the current step of it. In this way, the imaging performance information may be automatically updated and/or refreshed in accordance with a current deviation and/or current instructions to reduce the current deviation.

In an embodiment, the measurement data further may comprise a measurement of a current breathing activity of the subject, and wherein determining the current deviation between the actual position and the target position of at least the region of interest further may consider the current deviation caused by the breathing activity. For example, the device for carrying out the method and/or the medical imaging system carrying out the method may comprise suitable detection means, e.g. one or more of a breathing sensor, a camera, an infrared camera, etc., to detect the breathing activity of the subject. In this way, e.g. a breathing depth, exact timing of breath-holds and/or reaching the same breath-hold positions for multi-breath-hold image acquisitions, may be detected and/or determined, which are affecting or influencing factors for image quality.

According to an embodiment, the current deviation between the actual position and the target position may be determined over a period of time and then averaged before generating the imaging performance information. For example, a degree or level of compliance of the subject may be averaged over a few seconds to provide improved consistency in the one or more images communicated, e.g. visualized, to the subject over time. Still, the one or more images may demonstrate to the subject that its behavior largely affects or influences image quality. Effectively, the subject can see a stream of images as in a video with its quality influenced by its behavior in the last few seconds. Optionally, in order to provide some change of image content overtime, several adjacent slices of neighbored body parts will be displayed one after another, possibly similarly as actually acquired. The effect or influence of the motion of the subject on the one or more images may be determined, e.g. calculated, to be realistic, exaggerated, or underrepresented depending on the actual amount of motion of the patient. This ensures that image quality is, preferably always, on a minimum level such that the subject can at least recognize basic anatomical features in these images.

In an embodiment, the current deviation may be computed and/or considered, by the data processing unit, with at least one motion impact factor taking into account an impact or a degree of impact of a particular motion, a particular type of motion, and/or a motion of a particular body portion, e.g. a motion that affects or is expected to affect a specific region, of the subject on compliance with the positioning rule, and wherein the motion impact factor is further taken into account, by the data processing unit, to adjust a representation intensity of the imaging performance information before it is communicated to the subject. In other words, the at least one motion impact factor may amplify and/or highlight position deviation information for the communication, e.g. visualization, to the subject. This real-time feedback may highlight the position deviation of the body, i.e. region of interest, from the ideal position and overall compliance of the subject. Thereby, a more critical or most critical deviation may be selected as a "feedback-focus", because the subject might not be able to handle several aspects in parallel.

For example, the at least one motion impact factor may be related to one or more regions of interest, wherein the motion impact factor may indicate and/or differentiate, within the one or more regions of interest, between a motion-critical region of the subject's body and a non-motion-critical region of the subject's body. A degree of criticality of a specific region of interest may be associated with a workflow of the imaging procedure. These regions may, for example, be estimated and/or determined based on an optical detection of subject's position, from which it may be contemplated whether or not a motion confined to a specific region, e.g. body region, of the subject affects a predetermined imaging procedure or not. The estimation and/or determination may be based on a comparison with a respective threshold indicative for a degree of motion that is regarded as allowable or not allowable, respectively. Accordingly, the respective motion impact factor may be estimated and/or determined to be weighty or more weighty for a region whose motion noticeably affects image acquisition, and less weighty for another region whose motion affects image acquisition little, not significantly, or the like. In another example, breathing of the patient may be a further source of motion. Thereby, e.g. a breathing depth, an exact timing of breath-holds and/or reaching the same breath-hold positions for multi-breath-hold image acquisition or scans in a repeatable manner may be considered to affect one or more factors for the image quality. The impact factor may also be changed over time. Preferably it will be slowly increased over time to gently guide the subject towards more compliance.

Further, computing and/or considering the at least one motion impact factor may be used, by the data processing unit, to emphasize, e.g. visually highlight, the respective imaging performance information based on the motion impact factor. For example, information related to less impacting motion may be at least less emphasized, whereas information related to more impacting may be at least more emphasized. Emphasizing the information may comprise, for example, expressing through are stronger, e.g. more easily perceptible or, even if subjective, stronger, more accentuated, more insistent, etc., highlighting the information for the subject, e.g. in image form, in audio, etc.

According to an embodiment, the method may be carried out during real-time operation of the medical imaging system. For example, particularly the imaging performance information may be determined and provided to the subject during real-time operation of the medical imaging system. In this way, the subject is provided with the imaging performance information in a situation, i.e. during the imaging procedure and/or actual image acquisition, in which the subject's cooperation and/or involvement affects or is expected to affect the image quality.

In an embodiment, the medical imaging system may be selectively operated in an operational imaging mode and in a training and/or preparation mode preceding the operational imaging mode and in which imaging is not yet performed. Thereby, the method may further comprise:

during the training mode, obtaining, by the data processing unit, measurement data of at least the region of interest, from which the actual position of at least the region of interest is derivable;

during the training mode, determining, by the data processing unit, the current deviation between the actual position and the target position of at least the region of interest, by comparing the positioning rule with the obtained measurement data;

during the training mode, determining, by the data processing unit, whether or not the current deviation is within one or more boundary conditions; and during the training mode, communicating to the subject, by the data processing unit, whether or not the current deviation is within the one or more boundary conditions and/or a consequence this would have for the operational imaging mode.

In other words, during the training and/or preparation phase, the subject can test the method and learns also about the consequences of its behavior and/or cooperation and the acceptance ranges. For example, a rather small motion at an uncritical region might be compensated by the medical imaging system, e.g. by means of a correction algorithm or the like, and has no big impact on the imaging procedure or image quality. A rather critical motion at the region of interest might trigger a stop signal to terminate the current image acquisition, and may further require or trigger a restart with a delay and extension in the overall imaging procedure time. Further, boundary conditions for the different consequences associated with the subject's behavior and/or cooperation might be displayed in different colors and/or audio signals, and the subject on the one hand side learns to concentrate on the most important boundary conditions but may be informed about how its performing during the training phase and how fast and/or how the subject may adapt and follow the guidance, thereby providing an iterative optimization of the imaging procedure.

Accordingly, the data collected during the training and/or preparation phase may be used to optimize, by the data processing unit, the method and/or algorithm described herein. After the optional training and/or preparation phase, the optimized method and/or algorithm may be applied to medical imaging system during the operative imaging procedure. The visualization of the actual performance and a reference of the best possible image quality may also assist the subject to recognize how much improvement is possible.

According to a second aspect, there is provided a medical imaging system. comprising:

an imaging device;

a data processing unit; and at least one detection device, at least configured to capture at least a part of a subject to be imaged by the imaging device;

wherein the data processing unit is configured to:

determine a positioning rule, at least indicating, at least for a region of interest, one or more target positions, wherein a deviation between an actual position and the target position can affect imaging performance;

obtain, from the at least one detection device, measurement data of at least the region of interest, from which the actual position of at least the region of interest is derivable;

determine a current deviation between the actual position and the target position of at least the region of interest, by comparing the positioning rule with the obtained measurement data;

generate imaging performance information, at least indicating whether the current deviation between the actual position and the target position of at least the region of interest currently affects or is to affect the imaging performance or not; and provide the generated imaging performance information to be communicated to a subject to be imaged.

This provides the same or similar effect as discussed above with regard to the first aspect.

As used herein, the data processing unit may be any suitable computing means, such as a processor, a computer, or the like. It may comprise one or more of a data interface, a communication interface, etc.

The at least one detection means may comprise one or more of a motion detection sensor, a breathing detection sensor, a camera, an infrared camera, or the like. The at least one detection means may be operatively connected to at least the data processing unit to provide the measurement data thereto.

The imaging device may be configured, for example, for MRI, MR LINAC, PET-MR and other MR-hybrid systems.

According to an embodiment, wherein the medical imaging system further comprises a machine-subject communication device, configured to communicate the generated imaging performance information to the subject, and to utilize one or more of a visual communication, an audio communication, and a tactile communication. The communication device may be operatively connected to at least the data processing unit to receive the imaging performance information. For example, the communication device may comprise one or more of a display, a loudspeaker, headphone, or the like. In this way, the imaging performance information.

According to a third aspect, there is provided a computer program element, which when executed by a processor is configured to carry out the method of the first aspect, and/or to control a system according to the second aspect.

According to a fourth aspect, there is provided a computer-readable storage or transmission medium, which has stored or which carries the computer program element according to the third aspect.

It is noted that the above embodiments may be combined with each other irrespective of the aspect involved. Accordingly, the method may be combined with structural features of the system of the other aspects and, likewise, the system may be combined with features described above with regard to the method.

These and other aspects of the present invention will become apparent from and elucidated with reference to the embodiments described hereinafter.

BRIEF DESCRIPTION OF THE DRAWINGS

Exemplary embodiments of the invention will be described in the following drawings.

DETAILED DESCRIPTION OF EMBODIMENTS

Figure 1:
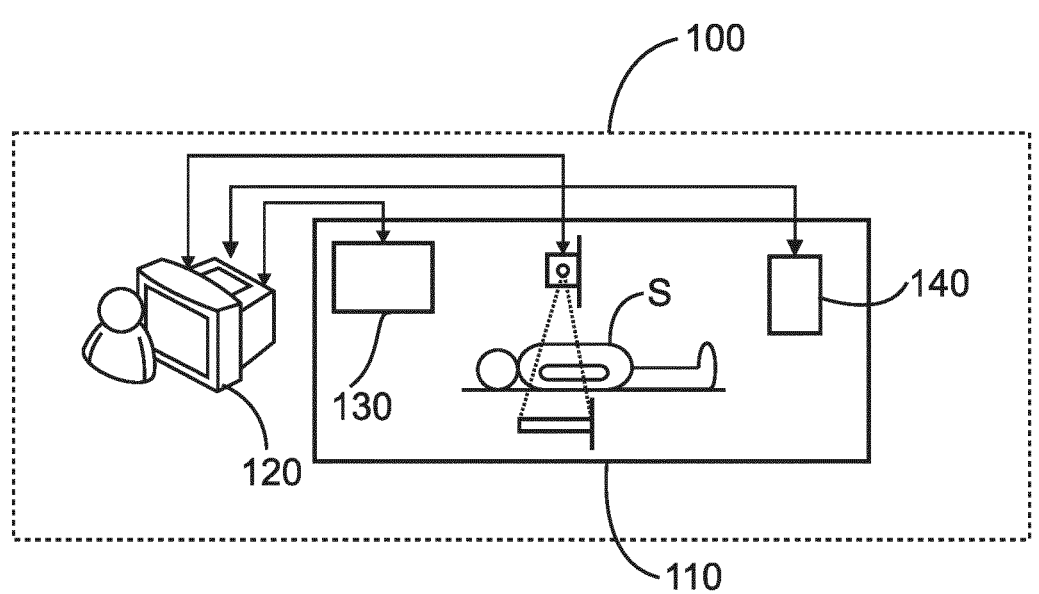
FIG. 1 shows in a schematic block diagram a medical imaging system according to an embodiment.

FIG. 1 shows in a schematic block diagram a medical imaging system 100, which may be utilize magnetic resonance imaging (MRI) technology.

The medical imaging system 100 comprises an imaging device 110, which is, for example, a MRI scanner as known in the art. Accordingly, in this exemplary embodiment, the imaging device 110 comprises a bore, a radiation source, a detector, etc. The medical imaging system 100 further comprises a data processing unit 120, which is operatively connected to the imaging device 110. It further comprises at least one detection device 130, which is at least configured to capture at least a part of a subject S, also referred to as a region of interest, to be imaged by the imaging device 110. For example, the at least one detection device 130 is arranged in a room in which the medical imaging system 100 is located and/or within the bore of the medical imaging system 100. The at least one detection device 130 comprises one or more of a camera, infrared camera, a motion sensor, a breathing detection sensor, or the like. Further, the medical imaging system 100 comprises at least one a machine-subject communication device 140, which is configured to utilize one or more of a visual communication, an audio communication, and a tactile communication. For example, the at least one communication device 140 comprises one or more of a display or monitor, a loudspeaker, a headphone, or the like. It is noted that the communication device 140 may be arranged within the bore (as exemplary shown in FIG. 1) or may be arranged also outside the bore provided that the subject S is able to recognize the information provided via the communication device 140.

In general, the medical imaging system 100 may be operated in a semi-autonomous operating mode or in a fully-autonomous operating mode, which means that at least a part of an imaging procedure carried out by utilizing the medical imaging system 100. Due to the degree of automation of the imaging procedure, there may be a training or preparation phase for the subject S, in which the subject S is informed about requirements directed to the subject S, wherein the requirements concern e.g. a behavior of the subject S during the imaging procedure, such as holding still, holding still at a particular step of the imaging procedure, changing its position for a particular step of the imaging procedure, holding its breath for a period of time and/or a particular step of the imaging procedure, breathing in a particular pattern, or the like.

The data processing unit 120 is configured, e.g. by utilizing a suitable calculation procedure and/or algorithm, to determine a positioning rule, which at least indicates, at least for a region of interest, one or more target positions to be taken by the subject S, wherein the one or more target positions may comply with the above requirements or desired behavior directed to the subject S. Thereby, a deviation between an actual position and the target position can affect the imaging performance during the imaging procedure. Accordingly, the position rule comprises information on one or more of the above requirements or desired behavior. For example, the positioning rule may comprise information that follows a sequence of steps of the intended imaging procedure.

Further, the data processing unit 120 is configured to obtain, from the at least one detection device 130, measurement data of at least the region of interest, from which the actual position of at least the region of interest is derivable. For example, the measurement data comprise one or more measurements associated with motion of e.g. the region of interest to be imaged, including motion caused by the breathing behavior of the subject S. The measurement data may comprise one or more images taken from the subject S, from which one or more images a position and/or a change of position, meaning a motion of the subject S, may be derived by one or more suitable image analysis techniques. In at least some embodiments, the measurement data comprises a measurement of a current breathing activity of the subject S, wherein determining the current deviation between the actual position and the target position of at least the region of interest further considers the current deviation caused by the breathing activity.

The data processing unit 120 is further configured to determine a current deviation between the actual position and the target position of at least the region of interest, by comparing the positioning rule with the obtained measurement data. For example, the positioning rule may comprise information about at which point, e.g. time point, of the imaging procedure in which position a specific part of the body and/or the region of interest should be.

The data processing unit 120 is further configured to generate an imaging performance information 121 (see FIG. 2), which at least indicates whether the current deviation between the actual position and the target position of at least the region of interest currently affects or is to affect the imaging performance or not. It is noted that the deviation may also be understood as a current motion of the subject S, affecting the imaging performance. Further, the imaging performance information is generated with a refresh rate adapted to the imaging procedure, wherein the refresh rate may depend on the current step of the imaging procedure, a weight of the current deviation in terms of its effect on the imaging procedure, etc.

Further, the data processing unit 120 is configured to provide the generated imaging performance information 121 (see FIG. 2) to be communicated to the subject S. Thereby, the generated imaging performance information is communicated by using the communication device 140.

Figure 2:
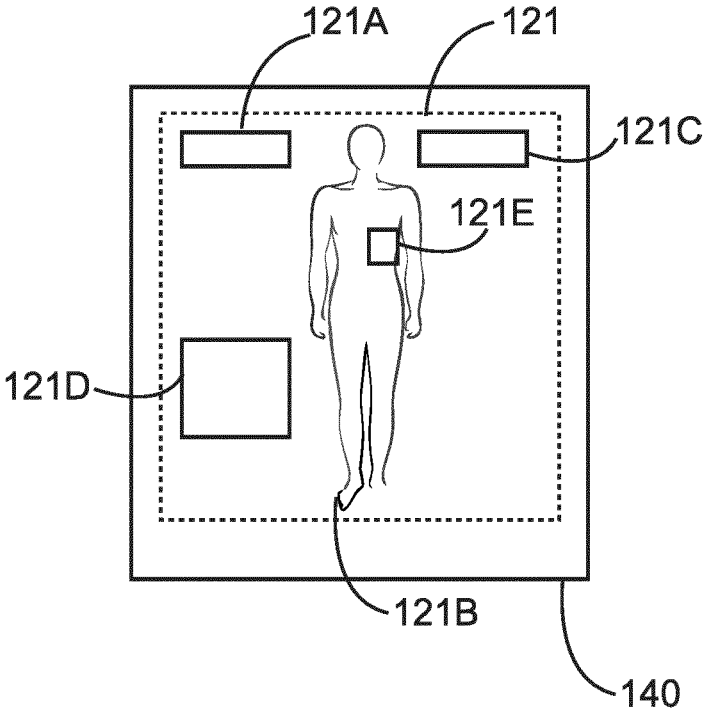
FIG. 2 shows a schematic representation of the imaging performance information according to an embodiment.

FIG. 2 shows a schematic representation of the imaging performance information 121 as it may be presented to the subject S via the communication device 140. It is noted that this representation may be varied in its degree of details, graphical illustration, etc. The imaging performance information 121 may also comprise other communication techniques, such as audio, tactile, or the like, so that the communication device 140 may alternatively or additionally comprise respective technical means, such as a loudspeaker, headphone, etc.

In at least some embodiments, the generated imaging performance information 121 comprises a first indicator 121A associated with an image quality of the imaging to be expected with the current deviation. For example, the image quality may be indicated by a quality value, by colors, wherein e.g. green may indicate sufficient quality and red may indicate insufficient quality, etc. Further, by way of example, in order to illustratively indicate and/or demonstrate the image quality, the generated imaging performance information for the case that the current deviation is maintained or at least not reduced to an allowed threshold, corresponding to e.g. a required minimum image quality, the imaging performance information 121 may comprise at least one artificial image 121B that is estimated and/or generated by the data processing unit 120. Thereby, the at least one artificial image 121B may be estimated from one or more pre-recorded images of the same or similar region of interest acquired at a previous subject. These one or more recorded images may be stored in a memory, database or the like (not shown). Further, these one or more images may be pre-recorded images of the same body part but from one or more other subjects, i.e. not from the presently examined subject S, which is difference is hardly noticeable for the subject S when viewing the communication device 140. For this purpose, one or more data manipulation techniques in k-space may be used to calculate a series of images with different levels of motion artefacts from one high quality base image. One of these images will be displayed at a time depending on the current level of motion and/or deviation from the desired and/or ideal position as specified in the positioning rule. Further, the current deviation between the actual position and the target position may be determined over a period of time and then averaged before generating the imaging performance information 121, and particularly the at least one artificial image 121B. For example, the level or degree of compliance and/or the deviation determined may be averaged over e.g. a few seconds to provide consistency in the at least one artificial image 121B over time. This may generate a stream of images as in a video with its quality influenced by the subject's S behavior in the last few seconds. In order to provide some change of image content over time, several adjacent slices of neighbored body parts may be displayed one after another, possibly similarly as actually acquired.

Alternatively or additionally, the generated imaging performance information 121 comprises a second indicator 121C associated with a scan time, e.g. a remaining scan time until completion of the imaging procedure, of the imaging procedure to be expected with the current deviation. For example, the second indicator 121C may be a value, and may optionally be highlighted by e.g. an illustrative color or the like, so as to indicate whether or not the current deviation affects the imaging procedure in a negative or positive manner.

Further, the generated imaging performance 121 may comprise one or more instructions 121D for one or more actions, which are configured to instruct the subject S to at least reduce the current deviation by carrying out the one or more actions. For example, the one or more instructions 121D may be determined, e.g. calculated, to instruct the subject S to hold still, breath in a specific pattern, etc.

Further, the current deviation may be computed with at least one motion impact factor taking into account an impact of a particular motion, a particular type of motion, and/or a motion of a particular body portion of the subject S on compliance with the positioning rule, and wherein the motion impact factor is further taken into account, to adjust an intensity of the imaging performance information 121 before it is communicated to the subject S. Based on the at least one motion impact factor, the visualization to the subject S may be amplified, e.g. highlighted, focus, etc., as indicated in FIG. 2 by a rectangle 121E. This real-time feedback highlights the position deviation of the body and/or region of interest from the ideal position and/or overall compliance. For example, a particularly critical deviation may selected as a "feedback-focus". Further based on the at least one motion impact factor, a dynamic display algorithm may focus on the most critical non-compliant performance and may give support information to go back on track, e.g. by using the one or more instructions 121D. This support information or instruction may be different for the different methods of being non-compliant. For breathing frequency synchronization and amplified audio signal with iterative adaptation of the frequencies guides the subject S to the target frequency. Further, motion may be displayed in an amplified way and the guidance should focus on body region—e.g. one special landmark on the knee that should be moved back to the target position. The communication device 140 may show mainly the simplified information to allow fast recognition and position matching supported by audio and/or visual information.

Figure 3:
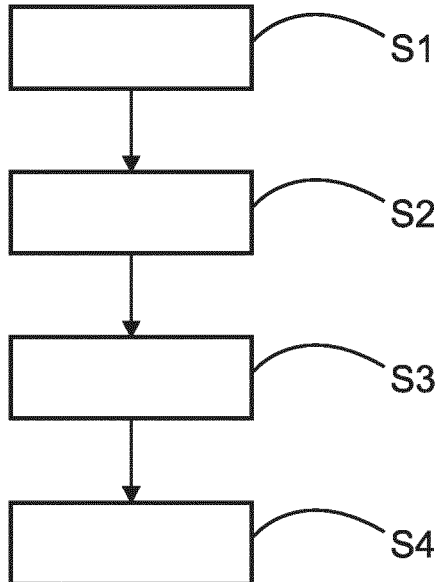
FIG. 3 shows in a flow chart a method for operating a medical imaging system according to an embodiment.

FIG. 3 shows in a flow chart a method for operating the medical system 100.

In a step S1, the data processing unit 120 determines the positioning rule, i.e. determines, e.g. selects, the positioning rule suitable and/or dedicated to the imaging procedure intended for the subject S.

In a step S2, the data processing unit 120 obtains the measurement data of at least the region of interest, from the at least one detection device 130, from which the actual position of at least the region of interest is derivable or derived, e.g. by determining the actual position by image analysis techniques, motion sensing, breathing sensing, etc.

In a step S3, the data processing unit 120 determines a current deviation between the actual position and the target position of at least the region of interest, by comparing the positioning rule with the obtained measurement data.

In a step S3, the data processing unit 120 generates the imaging performance information 121, at least indicating whether the current deviation between the actual position and the target position of at least the region of interest currently affects the imaging performance in terms of image quality and/or remaining imaging time or not, or is expected to affect the imaging performance in terms of image quality and/or remaining imaging time or not.

In a step S4, the data processing unit 120 provides the generated imaging performance information to be communicated to the subject S by utilizing the communication device 140, and using one or more, optionally different, communications techniques, such as visual, audio, tactile, etc.

Optionally, as explained above, the medical imaging system 100 is selectively operated in the training mode preceding the operational imaging mode. Optionally, the training mode may utilize another device (not shown) and/or another room separated to at least the imaging device 110, in order to perform the training mode for one subject and in parallel the actual imaging procedure for another subject.

During the training mode, the data processing unit 120 obtains the measurement data of at least the region of interest, from which the actual position of at least the region of interest is derivable. Further, during the training mode, the data processing unit 120 obtains the current deviation between the actual position and the target position of at least the region of interest, by comparing the positioning rule with the obtained measurement data. Further, during the training mode, the data processing unit 120 determines whether or not the current deviation is within one or more boundary conditions. Then, during the training mode, the data processing unit 120 communicates, via the communication device 140 or another communication device (not shown), whether or not the current deviation is within the one or more boundary conditions and/or a consequence this would have for the operational imaging mode. In other words, during the training mode, the subject S can test the above method and can learn about the consequences and the acceptance ranges when deviating from the positioning rule. Thereby, the boundary conditions for the different consequences might be displayed in different colors (audio signals) and the patient on the one hand side learns to concentrate on the most important parameters but he also can see how he is performing during the training phase and how fast/how good he can adapt and follow the guidance (iterative optimization). After the training mode, which may also be referred to as training phase or preparation phase, the optimized algorithm can be applied during the actual imaging procedure.

In another exemplary embodiment, a computer program or computer program element is provided that is characterized by being configured to execute the method steps of the method according to one of the preceding embodiments, on an appropriate system.

The computer program element might therefore be stored on a data processing unit, which might also be part of an embodiment. This data processing unit may be configured to perform or induce performing of the steps of the method described above. Moreover, it may be configured to operate the components of the above described device and/or system. The computing unit can be configured to operate automatically and/or to execute the orders of a user. A computer program may be loaded into a working memory of a data processor. The data processor may thus be equipped to carry out the method according to one of the preceding embodiments.

Further, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It is noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and the foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS

100 medical imaging system
110 imaging device
120 data processing unit
121 imaging performance information
130 detection means
140 communication device
Sx method step

The invention claimed is:

1. A method for operating a medical imaging system, comprising:
    determining, by a data processing unit, a positioning rule, at least indicating, at least for a region of interest, one or more target positions, wherein a deviation between an actual position and the target position can affect imaging performance;
    obtaining, by the data processing unit, measurement data of at least the region of interest, to derive the actual position of at least the region of interest;
    determining, by the data processing unit, a current deviation between the actual position and the target position of at least the region of interest, by comparing the positioning rule with the obtained measurement data;
    generating, by the data processing unit, imaging performance information, at least indicating whether the current deviation between the actual position and the target position of at least the region of interest currently affects the imaging performance in terms of image quality and/or remaining imaging time or not, or is expected to affect the imaging performance in terms of image quality and/or remaining imaging time or not; and providing, by the data processing unit, the generated imaging performance information to be communicated to a subject to be imaged.

2. The method of claim 1, wherein the generated imaging performance information comprises a first indicator associated with a measure of image quality of the imaging to be expected with the current deviation.

3. The method of claim 1, wherein the generated imaging performance information comprises a second indicator associated with a measure of scan time of the imaging to be expected with the current deviation.

4. The method of claim 1, wherein the generated imaging performance information comprises at least one artificial image estimated for the case that the current deviation is maintained or at least not reduced to an allowed threshold.

5. The method of claim 4, wherein the at least one artificial image is estimated from one or more pre-recorded images of the same or similar region of interest acquired at a previous subject.

6. The method of claim 1, wherein the generated imaging performance information comprises one or more instructions for one or more actions, computed to guide from the actual position causing the current deviation to the target position.

7. The method of claim 1, wherein providing the generated imaging performance information comprises visualizing the same for the subject.

8. The method of claim 1 wherein the imaging performance information is generated with a refresh rate adapted to a current stage of the imaging procedure.

9. The method of claim 1, wherein the measurement data further comprises a measurement of a current breathing activity of the subject, and wherein determining the current deviation between the actual position and the target position of at least the region of interest further considers the current deviation caused by the breathing activity.

10. The method of claim 1, wherein the current deviation between the actual position and the target position is determined over a period of time and then averaged before generating the imaging performance information.

11. The method of claim 1, wherein the current deviation is computed, by the data processing unit, with at least one motion impact factor taking into account an impact of a particular motion, a particular type of motion, and/or a motion of a particular body portion of the subject on compliance with the positioning rule, and wherein the motion impact factor is further taken into account, by the data processing unit, to adjust a representation intensity of the imaging performance information before it is communicated to the subject.

12. The method of claim 1, wherein the medical imaging system is selectively operated in an operational imaging mode and in a training mode preceding the operational imaging mode and in which imaging is not yet performed, and the method further comprises:

during the training mode, obtaining, by the data processing unit, measurement data of at least the region of interest, to derive the actual position of at least the region of interest;

during the training mode, determining, by the data processing unit, the current deviation between the actual position and the target position of at least the region of interest, by comparing the positioning rule with the obtained measurement data;

during the training mode, determining, by the data processing unit, whether or not the current deviation is within one or more boundary conditions; and during the training mode, communicating to the subject, by the data processing unit, whether or not the current deviation is within the one or more boundary conditions and/or a consequence this would have for the operational imaging mode.

13. A computer program element comprising executable instructions stored on a non-transitory computer readable medium, which when executed by a processor is configured to carry out the method of claim 1.

14. A medical imaging system, comprising:
an imaging device;
a data processing unit; and
at least one detection device, at least configured to capture at least a part of a subject to be imaged by the imaging device;
wherein the data processing unit is configured to:
determine a positioning rule, at least indicating, at least for a region of interest, one or more target positions, wherein a deviation between an actual position and the target position can affect imaging performance;
obtain, from the at least one detection device, measurement data of at least the region of interest, to derive the actual position of at least the region of interest;
determine a current deviation between the actual position and the target position of at least the region of interest, by comparing the positioning rule with the obtained measurement data;
generate imaging performance information, at least indicating whether the current deviation between the actual position and the target position of at least the region of interest currently affects or is to affect the imaging performance in terms of image quality and/or remaining imaging time or not; and
provide the generated imaging performance information to be communicated to a subject to be imaged.

15. The medical imaging system of claim 14, wherein the medical imaging system further comprises a machine-subject communication device, configured to communicate the generated imaging performance information to the subject, and to utilize one or more of a visual communication, an audio communication, and a tactile communication.

* * * * *